United States Patent [19]

Wagner

[11] 4,012,523

[45] Mar. 15, 1977

[54] HYPOLIPIDEMIC 2-(3,5-DI-TERT-BUTYL-4-HYDROXY-PHENYL)-(THIO OR SULFONYL) ALKANOIC ACIDS AND DERIVATIVES

[75] Inventor: Eugene R. Wagner, Midland, Mich.

[73] Assignee: The Dow Chemical Company, Midland, Mich.

[22] Filed: Nov. 22, 1974

[21] Appl. No.: 526,434

Related U.S. Application Data

[63] Continuation-in-part of Ser. No. 436,245, Jan. 24, 1974, abandoned, which is a continuation-in-part of Ser. No. 332,323, Feb. 14, 1973, abandoned.

[52] U.S. Cl. .............................. 424/308; 260/470; 260/448 R; 260/501.1; 260/515 M; 260/516; 424/317

[51] Int. Cl.$^2$ .............. A61K 31/19; A61K 31/235; C07C 65/00; C07C 149/40

[58] Field of Search .......... 424/308, 317; 260/470, 260/501.1, 515 M, 516

[56] References Cited

UNITED STATES PATENTS

| | | | |
|---|---|---|---|
| 2,681,363 | 6/1954 | Schwenk | 424/317 X |
| 3,249,632 | 5/1966 | Peterson | 260/473 G |
| 3,262,850 | 7/1966 | Jones | 260/473 G |
| 3,369,025 | 2/1968 | Bolhofer | 260/520 C X |
| 3,383,411 | 5/1968 | Schultz | 260/520 C X |
| 3,455,994 | 7/1969 | Knell | 260/473 G |
| 3,576,883 | 4/1971 | Neuworth | 424/337 X |
| 3,637,863 | 1/1972 | Braus | 260/609 F |
| 3,652,646 | 3/1972 | Leigh | 260/470 X |
| 3,674,836 | 7/1972 | Creger | 424/308 X |
| 3,707,549 | 12/1972 | Mills | 260/470 |
| 3,708,514 | 1/1973 | Murakami | 424/308 X |
| 3,717,669 | 2/1973 | Grant | 424/308 |
| 3,784,697 | 1/1974 | Nahm | 424/308 X |
| 3,786,100 | 1/1974 | Neuworth | 424/331 X |
| 3,795,691 | 3/1974 | Douglas | 424/308 X |
| 3,804,839 | 4/1974 | Dahm | 260/471 R |

*Primary Examiner*—Albert T. Meyers
*Assistant Examiner*—A. P. Fagelson
*Attorney, Agent, or Firm*—James W. Ambrosius

[57] ABSTRACT

2-(3,5-Di-tert-butyl-4-hydroxyphenyl)-(thio or sulfonyl) alkanoic acids and ester derivatives and pharmaceutically-acceptable salts thereof are disclosed; pharmaceutical compositions containing said compounds and methods of reducing plasma lipid levels in mammals are also provided.

62 Claims, No Drawings

HYPOLIPIDEMIC 2-(3,5-DI-TERT-BUTYL-4-HYDROXYPHENYL)-(THIO OR SULFONYL) ALKANOIC ACIDS AND DERIVATIVES

CROSS-REFERENCE TO RELATED APPLICATION

This application is a continuation-in-part of my copending application Ser. No. 436,245, filed Jan. 24, 1974, now abandoned which is a continuation-in-part of application Ser. No. 332,323, filed Feb. 14, 1973, now abandoned.

BACKGROUND OF THE INVENTION

This invention relates to novel 2-(3,5-di-tert-butyl-4-hydroxyphenyl)-(thio or sulfonyl) alkanoic acids and 2-(3,5-di-tert-butyl-4-hydroxyphenyl)-(sulfonyl) alkanoates (hereinafter referred to, for convenience, as "alkanoic acids") and compositions containing the same. This invention also relates to methods for reducing plasma lipid levels, especially cholesterol and triglycericide levels and, in particular, triglyclyceride levels using such alkanoic acids and ester derivatives thereof. triglyglyceride As established by various studies, it is recognized that cholesterol and triglycerides play a major role in the formation of atherosclerotic plaques by accelerating the deposition of blood lipids in the arterial wall. It has been discovered that representative compounds of the group herein disclosed are effective in reducing cholesterol levels, and particularly triglyceride levels in the blood of mammals. These activities make the compounds herein useful as compositions in ameliorating such conditions as atherosclerosis and other clinical entities in which the underlying etiology is associated with lipid imbalance or hyperlipidemia.

BRIEF SUMMARY OF THE INVENTION

The novel alkanoic acids and alkanoates with which the present invention is concerned are represented by the general formula:

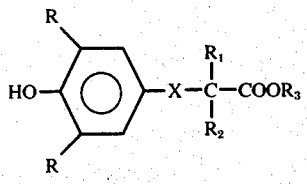

wherein:
 each R represents a tert-butyl group;
 X represents S or $SO_2$;
 $R_1$ represents hydrogen or methyl;
 $R_2$ represents an alkyl group of from one to about six carbon atoms;
 $R_3$ represents hydrogen or an alkyl group of from one to about three carbon atoms, with the proviso that when X is S, $R_3$ is hydrogen, or
the salts thereof formed with pharmaceutically acceptable bases. Methods of reducing plasma lipid levels in mammals with compounds of the above formula, as well as those wherein $R_3$ can also be an alkyl group as defined when X is S, are also included within the scope of the invention.

DETAILED DESCRIPTION OF THE INVENTION

In general, any base which will form an acid addition salt with a carboxylic acid and whose pharmacological properties will not cause an adverse physiological effect when ingested by the body systm is considered as being within the scope of this invention. Suitable bases thus include, for example, the alkali metal and alkaline earth metal hydroxides, carbonates, bicarbonates, etc., such as sodium hydroxide, potassium hydroxide, calcium hydroxide, potassium carbonate, sodium bicarbonate, magnesium carbonate and the like, ammonia, primary, secondary and tertiary amines and the like. Also, aluminum salts of the instant compounds may be obtained by treating the corresponding sodium salt with an appropriate aluminum complex such as aluminum chloride hexahydrate, etc. The acid addition salts thus obtained are the functional equivalent of the corresponding alkanoic acids and one skilled in the art will appreciate that the variety of acid addition salts embraced by this invention are limited only by the criterion that the bases employed in forming the salts be both non-toxic and physiologically acceptable.

The term "alkyl" as used in the specification and claims means both straight and branched chain alkyl radicals containing from 1 to about 6 carbon atoms, e.g., methyl, ethyl, propyl, isopropyl, butyl, isobutyl, t-butyl, amyl, hexyl and the like.

Preferred compounds and compositions of the above Formula I include those wherein X is sulfur. In another embodiment, compounds wherein X is sulfonyl are preferred. In a further embodiment, preferred compounds include those wherein $R_1$ is hydrogen. In still another embodiment, preferred compounds include those wherein $R_1$ is hydrogen, X is sulfur and $R_3$ is hydrogen. An additional preferred class of compounds includes those wherein $R_1$ is hydrogen, x is sulfonyl and $R_3$ is hydrogen. Still another preferred class of compounds includes those wherein $R_1$ is hydrogen, $R_2$ is selected from the group consisting of methyl, ethyl, butyl and n-pentyl, and $R_3$ is hydrogen. Still another preferred class of compounds are those wherein $R_3$ is alkyl and X is sulfonyl. Another class of compounds which are preferred are those wherein $R_1$ is methyl, X is sulfur and $R_3$ is hydrogen. A further preferred class includes compounds wherein $R_1$ is methyl, $R_2$ is selected from the group consisting of methyl, ethyl, n-pentyl and n-hexyl, $R_3$ is hydrogen and X is sulfur. Another preferred class of compounds includes those wherein $R_1$ is methyl, $R_3$ is alkyl and X is sulfonyl. Preferred compounds of the present invention include 2-((3,5-di-t.-butyl-4-hydroxyphenyl)thio)hexanoic acid and its pharmaceutically-acceptable acid addition salts.

The foregoing embodiments are also preferred as regards the methods of the present invention. An additional preferred embodiment for the methods of the present invention includes compounds wherein X is S and $R_3$ is alkyl. Still another such preferred embodiment includes compounds wherein X is $SO_2$ and $R_3$ is alkyl. A further such preferred embodiment includes compounds wherein $R_1$ is hydrogen, $R_3$ is alkyl and X is S. Another such preferred class of compounds includes those wherein $R_1$ is hydrogen, $R_2$ is n-propyl or n-butyl, $R_3$ is ethyl and X is sulfur. An additional class of preferred compounds includes those wherein X is $SO_2$ and $R_3$ is hydrogen.

The compounds of the present invention wherein X is sulfur can be prepared by reacting a 2,6-di-t.-butyl-4-mercaptophenol of the formula:

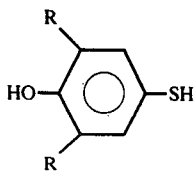

with a selected haloalkanoic acid or alkanoate reactant of the formula:

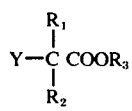

wherein, in the above formulas, Y is halogen such as bromo or chloro and each of R, $R_1$, $R_2$ are as previously defined and $R_3$ is hydrogen or alkyl. The reaction is ordinarily carried out in the presence of an inert liquid reaction medium, such as, for example, methanol, ethanol, propanol, t-butanol, benzene, dimethylformamide, toluene or the like, and a base, such as, for example, alkali metal and alkaline earth hydroxides, carbonates and the like. Representative of such bases are sodium hydroxide, potassium hydroxide, calcium hydroxide, potassium carbonate and the like. For compounds wherein $R_3$ is hydrogen, i.e., the acid derivatives, a ratio of about two moles of base per mole of phenol reactant is usually employed while equimolar amounts of base and phenol reactant are usually employed for compounds wherein $R_3$ is alkyl. Generally, equimolar amounts of the phenol and alkanoic acid or alkanoate reactants are employed. Compounds wherein $R_3$ is hydrogen, can, of course, be obtained by hydrolyzing the compounds wherein $R_3$ is alkyl with excess base.

In carrying out the reaction the phenol reactant is usually dispersed in a selected reaction medium and a solution of base added slowly thereto with stirring. During the base addition, the reaction mixture is usually cooled. Following the completion of the base addition, the alkanoic acid or alkanoate reactant is added to the reaction mixture and the resulting reaction mixture, which warms slightly due to exothermic reaction, is usually maintained, with stirring, at ambient temperatures for a period of from about 4 to 24 or more hours in order to allow for substantial completion of the reaction. Upon completion of the reaction period, the reaction mixture is acidified with aqueous hydrochloric acid and stirred. The resulting product precipitate, which is obtained by filtration of the reaction mixture, is washed with water and dried. The dried precipitate can be further purified if desired by recrystallizing the same from a suitable solvent such as, for example, ethanol, methylene chloride, hexane, chloroform or the like.

The compounds of the present invention wherein X is sulfonyl can be prepared by oxidizing the compounds of the present invention wherein X is sulfur with hydrogen peroxide in the presence of a water-miscible solvent such as glacial acetic acid or an alcohol, e.g., methanol, ethanol or the like. In carrying out the reaction, the 2-((3,5-di-tert-butyl-4-hydroxyphenyl)thio)alkanoic acid or ester reactant is dissolved in the selected water-miscible solvent and the resulting mixture is usually cooled to a temperature of from about 20° to about 30° C. Hydrogen peroxide is slowly added portionwise thereto with stirring, with a precipitate forming near the end of the hydrogen peroxide addition. Following the completion of the hydrogen peroxide addition, the reaction mixture is usually warmed slightly to redissolve the precipitate, and subsequently maintained at ambient temperatures for a period of from about 10 to about 20 hours. Subsequent mixing of the reaction mixture with ice water yields an oily product residue, which usually congeals upon stirring. The desired product residue can be recovered from the aqueous mixture and further purified according to the procedures set forth hereinabove.

The compounds of the present invention exhibit valuable pharmacological properties useful in the chemotherapeutic treatment of disorders and conditions associated with lipid imbalance or hyperlipidemia. Thus, in one embodiment of the present invention, methods of ameliorating conditions associated with hyperlipidemia are provided. In this respect, it has been discovered that many compounds of the class herein described exhibit hypocholesterolemic activity as well as unusually high hypotriglyceridemic activity. Such pronounced hypotriglyceridemic activity thus renders such compounds particularly useful in the chemotherapeutic treatment of pathological states characterized by high glyceride levels, i.e., hypertriglyceridemia. Thus, in another embodiment of the present invention, methods of treating hypertriglyceridemia are also provided.

For oral administration, pharmaceutical preparations of this invention may be made by following the conventional techniques of the pharmaceutical chemist. These techniques involve granulating and compressing when necessary or variously mixing and dissolving or suspending the ingredients as appropriate to the desired end product. Numerous pharmaceutical forms to carry the compounds can be used. For example, the pure compound can be used or it can be mixed with a solid carrier. Generally, inorganic pharmaceutical carriers are preferable and particularly solid inorganic carriers. One reason for this is the large number of inorganic materials which are known to be pharmaceutically safe and acceptable, as well as very convenient in preparing formulations. The compositions may take the form of tablets, linguets, powders, capsules, slurries, troches or lozenges and such compositions may be prepared by standard pharmaceutical techniques. Tablet compositions may be coated or uncoated and they may be effervescent or non-effervescent. Conventional excipients for tablet formations may be used. For example, inert diluents, such as magnesium carbonate or lactose, disintegrating agents such as maize starch or alginic acid, and lubricating agents such as magnesium stearate may be used.

If a liquid carrier is used, the preparation may be in the form of a soft gelatin capsule, a syrup, a liquid solution or suspension.

The hydrocarbon solubility of most of the compounds of this invention is high enough to allow the use of pharmaceutically-acceptable oils as carriers. For example vegetable or animal oils such as sunflower oil, safflower oil, maize oil or codliver oil can be used. Glycerine can also be used. With this latter solvent, from 2 to 30 percent water may be added. When water alone is the carrier, or when the solubility of the compound in the oil is low, the preparations can be administered in the form of a slurry.

Emulsion compositions may be formulated using emulsifying agents such as sorbitan tri-oleate, polyoxyethylene sorbitan monooleate, lecithin, gum acacia or gum tragacanth. Aqueous based suspensions may be prepared with the aid of wetting agents such as polyethylene oxide condensation products of alkylphenols, fatty alcohols or fatty acids with the suspending agents, for example a hydrophilic colloid such as polyvinylpyrrolidone. The emulsions and suspensions may contain conventional excipients such as sweeting agents, flowing agents, coloring materials and preservatives.

The compounds of this invention can also be incorporated in a nutritive foodstuff such as, for example, butter, margarine, edible oils, casein, carbohydrates and the like. Such nutritive compositions are adapted to be administered as a partial or total diet or as a supplement to the diet. Such compositions preferably contain from about 0.02 or less to about 2.0 or more percent of the active ingredient when administered as the total diet. The compositions can contain higher concentrations of the active ingredient when administered as a supplement.

For parenteral use, the compounds of this invention can be formulated with sterile ingredients, compounded and packaged aseptically. They may be administered intravenously or intramuscularly. Useful solvents for formulation in such use are the polyhydric aliphatic alcohols and mixtures thereof. Especially satisfactory are the pharmaceutically acceptable glycols, such as propylene glycol, and mixtures thereof. Glycerine is another example of a polyol which is particularly useful. Up to 25–30 percent by volume of water may be incorporated in the vehicle if desired. An 80 percent aqueous propylene glycol solution is a particularly convenient solvent system. A pH range, about 7.4, and isotonicity compatible with body isotonicity, is desirable. Basicity may be controlled by addition of a base as required, and a particularly convenient base is monoethanolamine. It may often be desirable to incorporate a local anaesthetic and such are well known to those skilled in the art.

The percentage of the compound to be used in the pharmaceutical carrier may be varied. It is necessary that the compound constitute a proportion such that a suitable dosage will be obtained and it is preferred to use pharmaceutical compositions containing at least 10 percent of the compound. Activity increases with concentration of the agent in the carrier, but those compositions containing a significant amount of carrier, e.g. at least 1 percent and preferably at least 5 percent, are preferred as they allow for the easier administration of the compound.

Generally, an effective daily dosage of the active ingredient can be from less than about 1 to about 100 milligrams or more per kilogram (mg./kg.) of body weight for most mammals. Dosage unit forms usually contain from about 1 to about 1000 mg., usually from about 1 to about 500 mg. of an active compound. One or more unit dosage forms are administered internally to a mammal to provide an active compound daily dosage level of from about 1 to about 4000 mg. or more.

However, it is not intended that the dosage regimens of the compounds or compositions be limited to any particular range. The dosage range desired in this invention is that range necessary to accomplish the desired end of lowering serum lipid levels. The amount of lipid level reduction desired will not be the same in all instances, but depends upon such factors as initial lipid level, predominance of one form of lipid over another, etc. The dosage, whether oral or parenteral must, therefore, of necessity be individually determined. Likewise, the concentration range of the compounds in the various formulations of this invention is not limited. The concentration should be high enough to avoid any excessive number of administrations per day, but low enough to allow flexibility in administration.

The active acid compounds and/or their corresponding esters or salts may be administered. In addition, other complementary hypolipidemic, hypocholesteremic or hypoglycemic agents as well as vitamins, analgesics, androgens, and the like compatible with the present compounds can be included in the present formulations to secure advantageous combination therapy. Moreover, preservatives, stabilizers, wetting agents, buffers, and the like can be incorporated, if desired, into the above formulations. Additionally, the formulations may also contain other therapeutically valuable substances.

The term "unit dosage form" as used in the specification and claims herein refers to physically discrete units suitable as unitary dosages, each unit containing a predetermined quantity of active material calculated to produce the desired therapeutic effect in association with the required pharmaceutical diluent, carrier or vehicle. The specification for the novel unit dosage forms of this invention is dictated by and directly dependent on (a) the unique characteristics of the active material and the particular therapeutic effect to be achieved and (b) the limitations inherent in the art of compounding such an active material for therapeutic use, as disclosed in detail in this specification, these being features of the present invention.

The invention will be more fully understood from the examples which follow. These examples are illustrative of the novel compounds of the invention as well as derivatives thereof employed in the claimed methods and are not to be construed as limiting the same.

EXAMPLE 1

A base solution (22 grams of NaOH in 41 milliliters (ml) of water) was added to a solution of 2,6-di-t-butyl-4-mercaptophenol (64.3 grams; 0.27 mole) in 540 ml. of absolute ethanol with stirring while cooling the reaction mixture under nitrogen. Following the base addition, a solution of 2-bromohexanoic acid (52.8 grams; 0.27 mole) in 27 ml. of ethanol was added and the resulting reaction mixture was stirred at room temperature for about 6 hours and left standing overnight. The reaction mixture was then diluted with about 400 ml. of water and acidified with cold 6N HCl. The yellow brown precipitate resulting from the acidification was obtained by filtration, washed with water and recrystallized from a methylenechloride-hexane mixture. As a result of these operations, the desired 2-((3,5-di-tert-butyl-4-hydroxyphenyl)thio)hexanoic acid compound was obtained as a white crystalline solid having a melting point of 140°–142° C. Analysis calculated for $C_{20}H_{32}O_3S$: C, 68.15; H, 9.14; S, 9.10. Found: C, 68.14; H, 9.34; S, 8.86.

EXAMPLE 2

2,6-Di-t-butyl-4-mercaptophenol (80.0 grams; 0.34 mole) was added to a stirred solution of sodium hydroxide (13.4 grams; 0.34 mole) in 500 ml. of 95% ethanol. To this mixture, ethyl-2-bromohexanoate (76.2 grams; 0.34 mole) was added and the resulting reaction mixture was allowed to warm slightly and then was stirred at ambient temperatures for a period of about 16 hours. The reaction mixture was subsequently poured into about 2500 ml. of 5% HCl with stirring. The oily layer formed upon acidification was separated from the reaction mixture and extracted with ethyl acetate. The extract was dried and evaporated to obtain a light brown oil representing the desired ethyl 2-((3,5-di-tert-butyl-4-hydroxyphenyl)-thio)hexanoate product having a boiling point of 190° C. at 5 mm. of Hg at about 95% purity.

EXAMPLE 3

The ethyl 2-((3,5-di-tert-butyl-4-hydroxyphenyl)thio)hexanoate product (75 grams; 0.195 mole) obtained in Example 2 was dispersed in 300 ml. of 95% ethanol and 500 ml. of 5N potassium hydroxide added thereto. The resulting reaction mixture was heated on a steam bath at the boiling point under gentle reflux for about 90 minutes with occasional stirring. Following the heating period, the reaction mixture was poured into 2000 ml. of 5% HCl with vigorous stirring. The white precipitate formed upon acidification was obtained by filtration and washed with water. Recrystallization (twice) of the precipitate from a methylene chloride-hexane mixture gave the desired 2-((3,5-di-tert-butyl-4-hydroxyphenyl)thio)hexanoic acid compound having a melting point of 140°–142° C.

In accordance with the procedures and teachings of Example 1 above, the following compounds can be prepared by employing the corresponding haloalkanoic acid reactants and, in the instances of salts, the corresponding bases:

2-((3,5-di-tert-butyl-4-hydroxyphenyl)thio)-propionic acid (melting at 111°–112° C.);

2-((3,5-di-tert-butyl-4-hydroxyphenyl)thio)-butyric acid (melting at 109°–111° C.);

2-((3,5-di-tert-butyl-4-hydroxyphenyl)thio)-heptanoic acid (melting at 85°–87° C.);

2-((3,5-di-tert-butyl-4-hydroxyphenyl)thio)-2-methyl-butyric acid (melting at 152°–153° C.);

2-((3,5-di-tert-butyl-4-hydroxyphenyl)thio)-2-methyl-octanoic acid (melting at 103°–105° C.);

sodium 2-((3,5-di-tert-butyl-4-hydroxyphenyl)-thio)-hexanoate (melting at 274°–282° C.);

2-((3,5-di-tert-butyl-4-hydroxyphenyl)thio)-2-methyl-pentanoic acid;

2-((3,5-di-tert-butyl-4-hydroxyphenyl)thio)-2-methyl-octanoic acid;

potassium 2-((3,5-di-tert-butyl-4-hydroxyphenyl)thio)-propionate; and calcium 2-((3,5-di-tert-butyl-4-hydroxyphenyl)thio)-heptanoate.

The above compounds can also be prepared according to Example 3 above if desired.

The following compounds are obtained in accordance with the procedures and teachings of Example 2 above by employing the corresponding haloalkanoate:

ethyl 2-((3,5-di-tert-butyl-4-hydroxyphenyl)-thio)-valerate (melting at 65°–66° C);

ethyl 2-((3,5-di-tert-butyl-4-hydroxyphenyl)-thio)-2-methyl-propionate;

propyl 2-((3,5-di-tert-butyl-4-hydroxyphenyl)-thio)-2-methyl-octanoate;

methyl 2-((3,5-di-tert-butyl-4-hydroxyphenyl)-thio)-2-methyl-propionate;

propyl 2-((3,5-di-tert-butyl-4-hydroxyphenyl)-thio)-2-methyl-valerate;

methyl 2-((3,5-di-tert-butyl-4-hydroxyphenyl)-thio)-propionate; and propyl 2-((3,5-di-tert-butyl-4-hydroxyphenyl)-thio)octanoate.

EXAMPLE 4

2-((3,5-Di-tert-butyl-4-hydroxyphenyl)thio)-hexanoic acid (10.0 grams), prepared as in Example 1 above, was dissolved in 150 ml. of glacial acetic acid by warming the solution to about 40° C and then cooled to about 25° C. Sixteen ml. of 30% hydrogen peroxide was slowly added, with stirring, thereto. Following the completion of the hydrogen peroxide addition, the reaction mixture was warmed to about 41° C to dissolve a white precipitate which had formed near the level of the hydrogen peroxide addition. The reaction mixture remained clear upon subsequent cooling to about 25° C. The reaction mixture was then stirred at ambient temperatures for a period of about 16 hours and thereafter poured into about 2500 ml. of ice water and the resulting aqueous mixture stirred. A white oily precipitate, which formed in the aqueous mixture and which congealed upon stirring, was recovered by filtration, washed with water and air-dried. The product thus obtained was mixed with 100 ml. of methylene chloride and about 350 ml. of hexane and the resulting cloudy solution was concentrated to a volume of about 400 ml. The concentrated solution was stirred until the temperature of the solution reached room temperature and allowed to stand for a few hours at ambient temperatures. The crystalline precipitate which formed upon standing was recovered by filtration, washed with hexane and dried. The foregoing recrystallization procedure was repeated and 7.95 grams of the desired 2-((3,5-di-tert-butyl-4-hydroxyphenyl)sulfonyl)-hexanoic acid compound was recovered as a crystalline solid having a melting point of 153°–154° C. Analysis — calculated for $C_{20}H_{32}SO_5$ (molecular weight 384.5)(percent): C, 62.47; H, 8.39; S, 8.34. Found (percent): C, 62.5; H, 8.14; S, 8.5.

In accordance with the procedure of Example 4 and the teachings of the specification, the following sulfonyl derivatives can be prepared by employing the corresponding 2-((3,5-di-tert-butyl-4-hydroxyphenyl)-thio)alkanoic acid or esters described hereinabove with respect to Examples 1–3:

2-((3,5-di-tert-butyl-4-hydroxyphenyl)sulfonyl)-propionic acid;

2-((3,5-di-tert-butyl-4-hydroxyphenyl)sulfonyl)-butyric acid;

2-((3,5-di-tert-butyl-4-hydroxyphenyl)sulfonyl)-heptanoic acid;

2-((3,5-di-tert-butyl-4-hydroxyphenyl)sulfonyl)-2-methylbutyric acid;

2-((3,5-di-tert-butyl-4-hydroxyphenyl)sulfonyl)-2-methyloctanoic acid;

sodium 2-((3,5-di-tert-butyl-4-hydroxyphenyl)-sulfonyl)hexanoate;

2-((3,5-di-tert-butyl-4-hydroxyphenyl)sulfonyl)-2-methylpentanoic acid;

2-((3,5-di-tert-butyl-4-hydroxyphenyl)sulfonyl)-2-methyloctanoic acid;

potassium 2-((3,5-di-tert-butyl-4-hydroxyphenyl)sulfonyl)propionate;

calcium 2-((3,5-di-tert-butyl-4-hydroxyphenyl)-sulfonyl)heptanoate;

ethyl 2-((3,5-di-tert-butyl-4-hydroxyphenyl)-sulfonyl)valerate;

ethyl 2-((3,5-di-tert-butyl-4-hydroxyphenyl)-sulfonyl)-2-methylpropionate;

propyl 2-((3,5-di-tert-butyl-4-hydroxyphenyl)-sulfonyl)-3-methyloctanoate;

methyl 2-((3,5-di-tert-butyl-4-hydroxyphenyl)-sulfonyl)-2-methylpropionate;

propyl 2-((3,5-di-tert-butyl-4-hydroxyphenyl)-sulfonyl)-2-methylvalerate;

methyl 2-((3,5-di-tert-butyl-4-hydroxyphenyl)-sulfonyl)propionate; and propyl 2-((3,5-di-tert-butyl-4-hydroxyphenyl)-sulfonyl)octanoate.

The hypolipidemic effect of the compounds of the invention is illustratively demonstrated in rats. In such procedures, the active test compound is dissolved in acetone, taken up on silica gel, and triturated with various aliquots of powdered feed until the desired concentration is reached. The feed mixture is then thoroughly mixed and fed to test groups of rats for a period of 14 days. Control groups of rats are similarly fed with untreated feed. Following the 14 day feeding period, the rats are sacrificed and the relative levels of serum cholesterol in blood samples determined by the Henly method (A. A. Henly, Analyst 82, 286 (1957)). The relative levels of triglyceride levels in blood samples are determined by the Van Handel and Zilversmit method (J. Lab. Clin. Med.; 50: 152 (1957)) and Clin. Chem., 7, 249 (1961)). Taking the average levels of the control mammals as standard, the mean results obtained in the treated groups is thereby ascertained.

The data presented in the following Table I indicate the mean decrease in serum cholesterol and serum triglyceride levels, as compared with the average levels of control mammals, obtained by separately feeding groups of rats medicated feeds containing 0.25% by weight of each of the indicated compounds for a period of about 14 days:

In other comparative operations, various oxygen analogs of the 2-((3,5-di-tert-butyl-4-hydroxyphenyl)-thio)alkanoic acids and esters were prepared and similarly tested for hypolipidemic activity. In such operations, feedstuffs containing the selected analogs at a concentration of 0.125% were fed to groups (6rats per group) of rats for a period of about 14 days and the cholesterol and triglyceride levels then determined as set forth hereinabove. The data obtained from such tests revealed that 2-(3,5-di-tert-butyl-4-hydroxyphenoxy)propionic acid was toxic at such concentration to all 6 rats in such test group while the 2-(3,5-di-tert-butyl-4-hydroxyphenoxy)butyric acid test compound was toxic to 2 of the 6 rats and produced a positive increase in the mean cholesterol and triglyceride levels (+7 and +36 percent, respectively) of the surviving members of the test group. 2-(3,5-di-tert-butyl-4-hydroxyphenoxy)-hexanoic acid was found to reduce the mean cholesterol and triglyceride levels by 7 and 36 percent, respectively. In comparative trials with the claimed 2-((3,5di-tert-butyl-4-hydroxyphenyl)thio)hexanoic acid at feed concentrations of 0.125% and 0.03%, respectively, reductions in the mean serum cholesterol and triglyceride levels of 33 and 67 percent, respectively, were obtained at the 0.125% concentration while reductions of 21 and 35 percent, respectively, were obtained with the 0.03% concentration. The sodium salt derivative of such compound similarly gave reductions of 27 and 72 percent, respectively, at the 0.125% feed concentration.

Such data clearly indicate the superior safeness and hypolipidemic activity of the claimed compounds.

In additional operations, test groups of male rats were administered a feed mixture containing 2-((3,5-di-tert-butyl-4-hydroxyphenyl)thio)hexanoic acid test compound at a concentration of 0.25% by weight. Certain of the rats were sacrificed 1, 2, 4, 7 and 14 days after initiation of the treatment and the serum triglyceride levels of the treated animals as compared with the control animals determined as previously set forth. Reductions in serum triglyceride levels of about 38%,

TABLE I

Decrease in Serum Lipid Levels with Feeds Containing 0.25% Active Ingredient As Compared with Control Groups

| Run No. | | Percent Decrease After 14 Days | |
|---|---|---|---|
| | | Cholesterol | Triglycerides |
| 1 | 2-((3,5-di-tert-butyl-4-hydroxyphenyl)thio)propionic acid | 32 | 80 |
| 2 | 2-((3,5-di-tert-butyl-4-hydroxyphenyl)thio)butyric acid | 37 | 76 |
| 3 | 2-((3,5-di-tert-butyl-4-hydroxyphenyl)thio)hexanoic acid | 29 | 70 |
| 4 | 2-((3,5-di-tert-butyl-4-hydroxyphenyl)thio)heptanoic acid | 24 | 52 |
| 5 | 2-((3,5-di-tert-butyl-4-hydroxyphenyl)thio)-3-methyl-propionic acid | 21 | 65 |
| 6 | 2-((3,5-di-tert-butyl-4-hydroxyphenyl)thio)-2-methyl-butyric acid | 32 | 80 |
| 7 | 2-((3,5-di-tert-butyl-4-hydroxyphenyl)thio)-2-methyl-heptanoic acid | 11 | 61 |
| 8 | 2-((3,5-di-tert-butyl-4-hydroxyphenyl)thio)-2-methyl-octanoic acid | 17 | 74 |
| 9 | ethyl 2-((3,5-di-tert-butyl-4-hydroxyphenyl)thio)valerate | 0 | 54 |
| 10 | ethyl 2-((3,5-di-tert-butyl-4-hydroxyphenyl)thio)hexanoate | 21 | 39 |
| 11 | ethyl 2-((3,5-di-tert-butyl-4-hydroxyphenyl)thio)-2-methyl-propionate | 23 | 60 |
| 12 | 2-((3,5-di-tert-butyl-4-hydroxyphenyl)sulfonyl)hexanoic acid | 18 | 45 |

The data presented in Table I clearly establish the effectiveness and usefulness of such compounds in treating hyperlipidemia in the blood of a mammal. Such data also show the pronounced hypotriglyceridemic effect of such compounds and the usefulness thereof in instances where predominantly high triglyceride levels exist.

54%, 65%, 70% and 77%, respectively, were obtained at the respective 1, 2, 4, 7 and 14 day intervals. Additional operations with the test compound indicate significant lowering of serum triglyceride levels were obtained at concentrations as low as 0.015 percent by weight of the compound in animal feeds.

Daily administration per os to male rats of the 2-((3,5-di-tert-butyl-4-hydroxyphenyl)thio)hexanoic acid test compound formulated in polyglycol 200 at dosage levels of 25, 50 and 100 mg/kg, respectively, over a 14 day period gave reductions in mean serum triglyceride levels of about 42%, 57% and 70%, respectively.

In other representative operations, separate groups of male rats were given daily oral doses of 200 and 400 mg/kg, respectively, of the 2-((3,5-di-tert-butyl-4-hydroxyphenyl)thio)hexanoic acid compound in a methocel or polyglycol carrier for a period of 14 days. Reductions in mean serum cholesterol and triglyceride levels of 30 and 62 percent, respectively, were obtained at the dosage rate of 200 mg/kg. while reductions of 38 and 69 percent, respectively, were obtained at the 400 mg/kg dosage rate.

In further operations, feedstuffs containing 0.25% 2-((3,5-di-tert-butyl-4-hydroxyphenyl)thio)hexanoic acid, 5% cholesterol and 1% cholic acid were administered to groups of male rats for a period of 14 days to induce hyperlipidemic. A comparison with control groups of rats indicate reductions in the mean serum cholesterol and triglyceride levels of 38 and 78 percent, respectively. Other test groups of male rats were maintained on a synthetic atherogenic diet containing the following:

| High Protein Casein | 20% |
| Sucrose | 41.993% |
| Peanut Oil | 20.0% |
| Cellulose (Fiber) | 7.0% |
| Salt Mix, Wesson | 4.0% |
| Cholesterol | 5.0% |
| Vitamin Mix | 1.0% |
| Cholic Acid | 1.0% |
| Zinc Carbonate | 0.06% | and 0.25% of the test compound for a period of 14 days. In these operations, reductions of the mean serum cholesterol and triglyceride levels of 68 and 30 percent, respectively, were obtained.

In other studies involving induced hyperlipemia conditions by diet control, groups of rabbits were maintained on a diet containing 0.5% 2-((3,5-di-tert-butyl-4-hydroxyphenyl)thio)hexanoic acid, 2% cholesterol and 6% corn oil for a period of eight weeks. During the eight week period, separate control groups of rabbits were maintained on a normal diet and on the cholesterol-corn oil diet only. During such 8 week period, a 2-5 fold elevation of serum triglyceride levels and a dramatic elevation of serum cholesterol levels from less than 100 mg/100 ml serum for the rabbits on a normal diet to a range of from about 3000 to more than 7000 mg/100 ml serum for the control rabbits fed the cholesterol and corn oil diet were observed. Measurement of the serum cholesterol and triglyceride levels of the test test groups maintained on the special diet including the test compound indicated mean reductions in such levels of 80 and 34 percent respectively, after two weeks; 81 and 61 percent respectively, after four weeks; 94 and 48 percent respectively, after six weeks; and 95 and 68 percent respectively, after eight weeks.

The following examples illustrate the preparation of pharmaceutical compositions of the present invention, but are by no means the sole methods of producing the same.

EXAMPLE 5

One thousand capsules for oral administration, each containing 100 mg. of 2-((3,5-di-tert-butyl-4-hydroxyphenyl)thio)hexanoic acid, can be prepared from the following ingredients:

| | Grams |
|---|---|
| 2-((3,5-di-tert-butyl-4-hydroxyphenyl)-thio)hexanoic acid | 100 |
| Lactose, U.S.P. | 100 |
| Starch, U.S.P. | 30 |
| Talc, U.S.P. | 6.5 |
| Calcium Stearate | 2.5 |

The active ingredient is powdered and mixed with the starch-lactose mixture followed by the talc and calcium stearate. The final mixture is then encapsulated in the usual manner employing hard gelatin capsules of appropriate size.

EXAMPLE 6

Two thousand tablets for oral use, each containing 1,000 mg. of active ingredient are prepared from the following ingredients:

| | Grams |
|---|---|
| 2-((3,5-di-tert-butyl-4-hydroxyphenyl)-thio)propionic acid | 2000 |
| Starch, U.S.P. | 140 |
| Talc, U.S.P. | 100 |
| Calcium Stearate | 14 |

The active ingredient is powdered and granulated with a 4% w/v aqueous solution of methylcellulose U.S.P. (1500 cps.). To the dried granules is added a mixture of the remainder of the ingredients and the final mixture slugged. The slugs are broken down by forcing through a screen and the resulting granules then compressed into tablets of proper weight.

EXAMPLE 7

An injectable preparation is made from the following ingredients to contain 100 mg. of the 2-((3,5-di-tert-butyl-4-hydroxyphenyl)thio)hexanoic acid active ingredient per ml:

| | Percent w/v |
|---|---|
| Sodium carboxymethylcellulose (low viscosity) | 0.5 |
| Tween 80 (polyoxyethylene sorbitan monooleate) | 0.4 |
| Sodium chloride | 0.9 |
| Benzyl alcohol | 0.9 |
| Active ingredient | 10.0 |
| Sterile distilled water, q.s., 1000.0 ml. | |

The previously sterilized active ingredient is homogenized with the already mixed and sterilized vehicle.

The 2,6-di-tert-butyl-4-mercaptophenol reactant, the haloalkanoic acid and haloalkanoate reactants are known and are readily available or can be prepared according to known or analogous procedures. For details, see Organic Reactions, vol. III, chapter 6, by Roger Adams et al; also the article by Muller et al., entitled "Untersuchungen an schwefelhaltigen Aroylen mittels der Electronenresonanz" in Liebig's Annalen (1961, Bd. 645, p. 79), and U.S. Pat. No. 3,129,262.

I claim:

1. A compound of the formula:

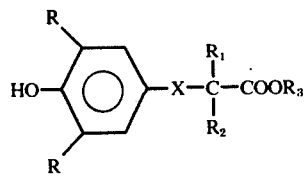

wherein
each R represents a tert-butyl group;
X represents S or SO₂;
R₁ is hydrogen or methyl;
R₂ represents an alkyl group containing from 1 to about 6 carbon atoms;
R₃ represents hydrogen or an alkyl group containing from 1 to about 3 carbon atoms with the proviso that when X is S, R₃ is hydrogen, or the pharmaceutically-acceptable acid addition salts thereof.

2. The compound of claim 1 wherein R₁ is hydrogen or the pharmaceutically acceptable acid salts thereof.

3. The compound of claim 1 wherein X is sulfur or the pharmaceutically acceptable acid addition salts thereof.

4. The compound of claim 1 wherein X is SO₂ or the pharmaceutically acceptable acid addition salts thereof.

5. The compound of claim 4 which is 2-((3,5-di-tert-butyl-4-hydroxyphenyl)sulfonyl)hexanoic acid.

6. The compound of claim 1 wherein R₁ is hydrogen, X is sulfur, R₃ is hydrogen or the pharmaceutically-acceptable acid addition salts thereof.

7. The compound of claim 6 wherein R₁ is hydrogen, R₂ is selected from the group consisting of methyl, ethyl, n-butyl and n-pentyl, R₃ is hydrogen or the pharmaceutically-acceptable acid addition salts thereof.

8. The compound of claim 6 which is 2-((3,5-di-tert-butyl-4-hydroxyphenyl)thio)propionic acid.

9. The compound of claim 6 which is 2-((3,5-di-tert-butyl-4-hydroxyphenyl)thio)butyric acid.

10. The compound of claim 6 which is 2-((3,5-di-tert-butyl-4-hydroxyphenyl)thio)hexanoic acid.

11. The compound of claim 6 which is 2-((3,5-di-tert-butyl-4-hydroxyphenyl)thio)heptanoic acid.

12. The compound of claim 6 which is sodium 2-((3,5-di-tert-butyl-4-hydroxyphenyl)thio)hexanoate.

13. The compound of claim 1 wherein R₁ is methyl, X is sulfur, R₃ is hydrogen or the pharmaceutically-acceptable addition salts thereof.

14. The compound of claim 13 wherein R₂ is selected from the group consisting of methyl, ethyl, n-pentyl and n-hexyl.

15. The compound of claim 14 which is 2-((3,5-di-tert-butyl-4-hydroxyphenyl)thio)-2-methyl-propionic acid.

16. The compound of claim 14 which is 2-((3,5-di-tert-butyl-4-hydroxyphenyl)thio)-2-methyl-butyric acid.

17. The compound of claim 14 which is 2-((3,5-di-tert-butyl-4-hydroxyphenyl)thio)-2-methyl-heptanoic acid.

18. The compound of claim 14 which is 2-((3,5-di-tert-butyl-4-hydroxyphenyl)thio)-2-methyl-octanoic acid.

19. A hypolipidemic composition comprising a hypolipidemically effective amount of a compound having the formula:

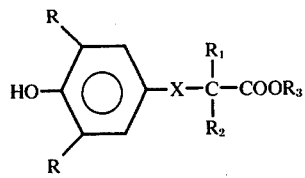

wherein
each R represents a tert-butyl group;
X is sulfur or SO₂;
R₁ is hydrogen or methyl;
R₂ represents an alkyl group containing from 1 to about 6 carbon atoms;
R₃ represents hydrogen or an alkyl group containing from 1 to about 3 carbon atoms with the proviso that when X is S, R₃ is hydrogen, or a pharmaceutically-acceptable acid addition salt thereof together with a pharmaceutical carrier therefor.

20. The composition of claim 19 wherein R₁ is hydrogen.

21. The composition of claim 19 wherein X is sulfur.

22. The composition of claim 19 wherein R₁ is hydrogen, X is sulfur, R₃ is hydrogen or the pharmaceutically-acceptable acid addition salts of the compound.

23. The composition of claim 22 wherein R₁ is hydrogen, R₂ is selected from the group consisting of methyl, ethyl, n-butyl and n-pentyl, R₃ is hydrogen or the pharmaceutically-acceptable acid addition salts of the compound.

24. The composition of claim 22 wherein the compound is 2-((3,5-di-tert-butyl-4-hydroxyphenyl)thio)-propionic acid.

25. The composition of claim 22 wherein the compound is 2-((3,5-di-tert-butyl-4-hydroxyphenyl)thio)-butyric acid.

26. The composition of claim 22 wherein the compound is 2-((3,5-di-tert-butyl-4-hydroxyphenyl)thio)-hexanoic acid.

27. The composition of claim 22 wherein the compound is 2-((3,5-di-tert-butyl-4-hydroxyphenyl)thio)-heptanoic acid.

28. The composition of claim 22 wherein the compound is sodium 2-((3,5-di-tert-butyl-4-hydroxyphenyl)thio)hexanoate.

29. The composition of claim 19 wherein R₁ is methyl, X is sulfur, R₃ is hydrogen or the pharmaceutically-acceptable addition salts of the compound.

30. The composition of claim 19 wherein R₂ is selected from the group consisting of methyl, ethyl, n-pentyl and n-hexyl.

31. A method for treating hyperlipidemia in the blood of a mammal which comprises internally administering to said mammal a hypolipidemically effective amount of a compound having the formula:

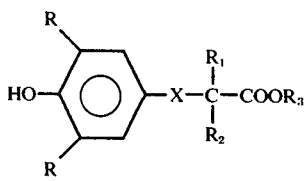

wherein
each R represents a tert-butyl group;
X represents sulfur or $SO_2$;
$R_1$ is hydrogen or methyl;
$R_2$ represents an alkyl group containing from 1 to about 6 carbon atoms;
$R_3$ represents hydrogen or an alkyl group containing from 1 to about 3 carbon atoms, or the pharmaceutically-acceptable acid addition salts thereof.

32. The method of claim 31 wherein the compound employed is one where $R_3$ is hydrogen.

33. The method of claim 31 wherein the compound employed is one where X is sulfur.

34. The method of claim 31 wherein the compound employed is one where $R_1$ is hydrogen, X is sulfur, $R_3$ is hydrogen or the pharmaceutically-acceptable salts thereof.

35. The method of claim 34 wherein the compound employed is one where $R_2$ is selected from the group consisting of methyl, ethyl, n-butyl and n-pentyl.

36. The method of claim 34 wherein the compound employed is 2-((3,5-di-tert-butyl-4-hydroxyphenyl)thio)-propionic acid.

37. The method of claim 34 wherein the compound employed is 2-((3,5-di-tert-butyl-4-hydroxyphenyl)thio)-butyric acid.

38. The method of claim 34 wherein the compound employed is 2-((3,5-di-tert-butyl-4-hydroxyphenyl)thio)-hexanoic acid.

39. The method of claim 34 wherein the compound employed is 2-((3,5-di-tert-butyl-4-hydroxyphenyl)thio)-heptanoic acid.

40. The method of claim 34 wherein the compound employed is sodium 2-((3,5-di-tert-butyl-4-hydroxyphenyl)-thio)hexanoate.

41. The method of claim 31 wherein the compound is administered orally.

42. The method of claim 31 wherein the compound employed is one where X is $SO_2$.

43. The method of claim 42 wherein the compound employed is one where $R_3$ is hydrogen.

44. The method of claim 43 wherein the compound employed is 2-((3,5-di-tert-butyl-4-hydroxyphenyl)sulfonyl)hexanoic acid.

45. A method of treating hypertriglyceridemia in the blood of a mammal comprising internally administering to said mammal a hypotriglyceridemically effective amount of a compound having the formula:

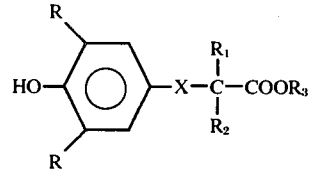

wherein
each R represents a tert-butyl group;
X is sulfur or $SO_2$;
$R_1$ is hydrogen or methyl;
$R_2$ represents an alkyl group containing from 1 to about 6 carbon atoms;
$R_3$ represents hydrogen or an alkyl group containing from 1 to about 3 carbon atoms, or a pharmaceutically-acceptable acid addition salt thereof.

46. The method of claim 45 wherein the compound employed is one where $R_1$ is hydrogen, $R_2$ is selected from the group consisting of methyl, ethyl, n-butyl and n-pentyl, $R_3$ is hydrogen or the pharmaceutically acceptable salts thereof.

47. The method of claim 46 wherein the compound employed is 2-((3,5-di-tert-butyl-4-hydroxyphenyl)thio)-propionic acid.

48. The method of claim 46 wherein the compound employed is 2-((3,5-di-tert-butyl-4-hydroxyphenyl)thio)-butyric acid.

49. The method of claim 46 wherein the compound employed is 2-((3,5-di-tert-butyl-4-hydroxyphenyl)thio)-hexanoic acid.

50. The method of claim 46 wherein the compound employed is 2-((3,5-di-tert-butyl-4-hydroxyphenyl)thio)-heptanoic acid.

51. The method of claim 46 wherein the compound employed is sodium 2-((3,5-di-tert-butyl-4-hydroxyphenyl)thio)-hexanoate.

52. The method of claim 46 wherein the compound is administered orally.

53. The method of claim 45 wherein the compound employed is one where $R_1$ is hydrogen, X is sulfur and $R_3$ is alkyl.

54. The method of claim 53 wherein the compound employed is one where $R_2$ is selected from the group consisting of n-propyl and n-butyl and $R_3$ is ethyl.

55. The method of claim 53 wherein the compound employed is ethyl 2-((3,5-di-tert-butyl-4-hydroxyphenyl)-thio)valerate.

56. The method of claim 53 wherein the compound employed is ethyl 2-((3,5-di-tert-butyl-4-hydroxyphenyl)-thio)hexanoate.

57. The method of claim 45 wherein the compound employed is one where $R_1$ is methyl, X is sulfur, $R_3$ is hydrogen or the pharmaceutically-acceptable addition salts thereof.

58. The method of claim 57 wherein the compound employed is one where $R_2$ is selected from the group consisting of methyl, ethyl, n-pentyl and n-hexyl.

59. The method of claim 45 wherein the compound employed is one where $R_1$ is methyl, X is sulfur and $R_3$ is alkyl.

60. The method of claim 45 wherein the compound employed is one where X is $SO_2$.

61. The method of claim 60 wherein the compound employed is one where $R_3$ is hydrogen.

62. The method of claim 61 wherein the compound employed is 2-((3,5-di-tert-butyl-4-hydroxyphenyl)sulfonyl)hexanoic acid.

* * * * *